United States Patent
Hanson et al.

(10) Patent No.: US 12,242,766 B2
(45) Date of Patent: Mar. 4, 2025

(54) SYSTEM AND METHOD FOR DECREASING DATA TRANSFER BETWEEN COMPUTING DEVICES

(71) Applicant: ShareSafe Media, LLC, Mobile, AL (US)

(72) Inventors: Robert B. Hanson, Mobile, AL (US); Dean Kei Naritoku, Mobile, AL (US); Peter Pronovost, Novelty, AL (US); Taylor Ann Peake, Birmingham, AL (US); Matthew Frank Clark, Birmingham, AL (US); Emily Leithauser Hart, Bessemer, AL (US)

( * ) Notice: Subject to any disclaimer, the term of this patent is extended or adjusted under 35 U.S.C. 154(b) by 0 days.

(21) Appl. No.: 18/696,788

(22) PCT Filed: Oct. 1, 2022

(86) PCT No.: PCT/US2022/045477
§ 371 (c)(1),
(2) Date: Mar. 28, 2024

(87) PCT Pub. No.: WO2023/056076
PCT Pub. Date: Apr. 6, 2023

(65) Prior Publication Data
US 2024/0402973 A1 Dec. 5, 2024

Related U.S. Application Data

(60) Provisional application No. 63/251,538, filed on Oct. 1, 2021.

(51) Int. Cl.
*G06F 3/14* (2006.01)
*G16H 10/60* (2018.01)

(52) U.S. Cl.
CPC ........... *G06F 3/1423* (2013.01); *G16H 10/60* (2018.01)

(58) Field of Classification Search
CPC ............ G06F 3/1423; G06F 3/14; G06F 3/00; G16H 10/60; G16H 10/40
See application file for complete search history.

(56) References Cited

U.S. PATENT DOCUMENTS

2004/0078832 A1* 4/2004 Yang ................ H04N 21/41415
725/151
2018/0046424 A1* 2/2018 Jo ........................ G09G 3/2096
(Continued)

*Primary Examiner* — Pegeman Karimi
(74) *Attorney, Agent, or Firm* — AdamsIP, LLC; Edward Brinkley Garner, III; James Hunter Adams

(57) ABSTRACT

A system and method for securely displaying patient data within a plurality of display windows of a display is provided. Additionally, the system is configured to reduce the amount of data transferred between the various computing devices in order to reduce strain on a network. The system generally comprises a first computing device having a first user interface, second computing device having a second user interface, processor operably connected to said first computing device and said second computing device, display operably connected to said processor, and non-transitory computer-readable medium coupled to said processor and having instructions stored thereon. The display is configured to receive image data from the first computing device and second computing device and present said image data via a display user interface, wherein said image data pertains to a plurality of application windows of the first user interface and second user interface.

27 Claims, 11 Drawing Sheets

(56) References Cited

U.S. PATENT DOCUMENTS

2020/0137140 A1\* 4/2020 Laukkanen ........... H04L 67/535
2022/0150575 A1\* 5/2022 Strain, Jr. ........ H04N 21/43072

\* cited by examiner

SYSTEM AND METHOD FOR DECREASING DATA TRANSFER BETWEEN COMPUTING DEVICES

CROSS REFERENCES

This application claims priority to U.S. Provisional Application Ser. No. 63/251,538, filed on Oct. 1, 2021, in which application is incorporated herein in its entirety by reference.

FIELD OF THE DISCLOSURE

The subject matter of the present disclosure refers generally to a system and method for decreasing the amount of data transferred between computing devices.

BACKGROUND

Healthcare facilities are increasingly focusing on enhancing a patient's treatment experience by way of technology. This allows said healthcare facilities to differentiate their services from those of competing healthcare facilities as well as improve patient satisfaction ratings, which may increase the number of patients who choose their services over said competing healthcare facilities. In particular, by investing in technology that improves nurse/patient interaction, increases safety, reduces readmissions, and reduces cost to the patient, healthcare facilities have greatly increased quality of care and efficiency of the workforce without also greatly increasing costs. For instance, healthcare facilities are already using televisions as a way to assist patients in learning about their conditions. Interactive patient education systems (video on-demand and/or Internet-enabled units) are becoming integral to the patient and staff satisfaction standards in healthcare facilities. And as regulatory requirements continue to quickly evolve, it is inevitable that these on-demand education systems will become a standard feature of hospitals instead of a value add to the patient experience. The fact that these types of technological improvements already improve efficiency of healthcare facility personnel will likely be enough to encourage the quick acceptance of these improvements even without regulatory obligation.

As these new technologies are introduced into healthcare environments, healthcare professionals must continue to figure out new ways to use said technologies to assist with day-to-day tasks, such using technology to assist with the discussion of medical procedure results, including, but not limited to, X-rays, EKGs, labs, etc. As healthcare facilities have become more digitized, so has the form of the various medical procedure results. This is convenient in that a healthcare professional may quickly access results so long as they have a computing device that has access to the Electronic Health Record containing the desired information, but it also can prevent emotional interaction with the patient that may cause the healthcare professional to come off as cold. Reducing the amount of information visually available to the patient may also reduce the patient's understanding about a diagnosis and how said diagnosis may be corrected. For instance, a healthcare professional looking at a screen while a patient watches said healthcare professional look at said screen does nothing to assist a patient in understanding their condition. Further, smaller screens have been shown to reduce neural activity and attention, meaning that simply allowing patients to view information about their condition on a mobile device may have little impact on their understanding.

On the other hand, sharing data in a way that is more interactive can create a bandwidth issue since this tends involve the transfer of video data. Bandwidth issues can be particularly devastating for smaller networks with many users needing to transmit large amounts across said smaller networks at the same time. When the amount of data being transferred exceeds the amount of available bandwidth, users may experience extreme buffering times or very low quality, greatly decreasing the user experience. This is particularly bad if a healthcare professional is trying to interact with a patient. Not only does this potentially increase the anxiety of the patient as they wait for results but decreases the efficiency in which said healthcare professional can interact with patients, which ultimately increases cost.

Accordingly, there is a need in the art for a system and method that may allow a healthcare professional to securely and quickly access data of an EHR while decreasing the amount of data transferred while interacting with a patient.

SUMMARY

A system and method for managing data transferred between computing entities is provided. In one aspect, the system is designed to allow for application windows of a computing device to be displayed within a display user interface of a display. In another aspect, the system is design to minimize the bandwidth required for communication between the computing device and the display by managing which application windows are actively mirrored/streamed from a computing device to the display. In yet another aspect, the system is designed to facilitate communication between users, especially when those users are healthcare professionals and patients. In yet another aspect, the system is configured to manage a queue of the system that assists healthcare professionals in communicating efficiently with patients. Generally, the system and methods of the present disclosure are designed to enhance communication between a patient and the patient's healthcare provider while reducing data bandwidth required for said communication.

The system generally comprises a first computing entity having a first user interface, second computing entity having a second user interface, at least one display having a display user interface, processor operably connected to said first computing device, second computing device, and display, and non-transitory computer-readable medium coupled to said processor and having instructions stored thereon. In one preferred embodiment, a database may be operably connected to the processor and the various data of the system may be stored therein, including, but not limited to, user data, patient data, and image data. In some preferred embodiments, a third computing device may be used by a third user to enter a display into a queue in order to connect users of the system via a communication window. A camera may be used to capture image data that may be transferred between one or more displays. A plurality of display windows of the display user interface preferably present application windows of the user interfaces of the computing devices. A control board of the display may be configured to receive said image data. In yet another preferred embodiment, a wireless communication interface may allow the processors of the system to receive and transmit image data therebetween.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other systems for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For instance, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises", and grammatical equivalents thereof are used herein to mean that other components, steps, etc. are optionally present. For instance, a system "comprising" components A, B, and C can contain only components A, B, and C, or can contain not only components A, B, and C, but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility). As will be evident from the disclosure provided below, the present invention satisfies the need for a system and method capable of reducing data transferred between computing devices.

Figure 1:
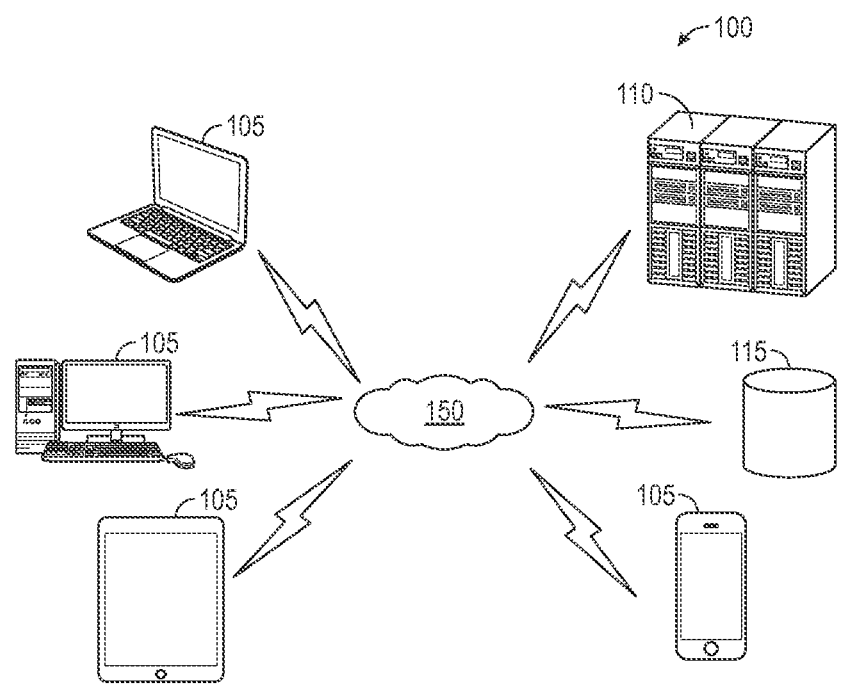
FIG. 1 illustrates a system embodying features consistent with the principles of the present disclosure.

FIG. 1 depicts an exemplary environment 100 of the system 400 consisting of clients 105 connected to a server 110 and/or database 115 via a network 150. Clients 105 are devices of users 405 that may be used to access servers 110 and/or databases 115 through a network 150. A network 150 may comprise of one or more networks of any kind, including, but not limited to, a local area network (LAN), a wide area network (WAN), metropolitan area networks (MAN), a telephone network, such as the Public Switched Telephone Network (PSTN), an intranet, the Internet, a memory device, another type of network, or a combination of networks. In a preferred embodiment, computing entities 200 may act as clients 105 for a user 405. For instance, a client 105 may include a personal computer, a wireless telephone, a streaming device, a "smart" television, a personal digital assistant (PDA), a laptop, a smart phone, a tablet computer, or another type of computation or communication interface 280. Servers 110 may include devices that access, fetch, aggregate, process, search, provide, and/or maintain documents. Although FIG. 1 depicts a preferred embodiment of an environment 100 for the system 400, in other implementations, the environment 100 may contain fewer components, different components, differently arranged components, and/or additional components than those depicted in FIG. 1. Alternatively, or additionally, one or more components of the environment 100 may perform one or more other tasks described as being performed by one or more other components of the environment 100.

As depicted in FIG. 1, one embodiment of the system 400 may comprise a server 110. Although shown as a single server 110 in FIG. 1, a server 110 may, in some implementations, be implemented as multiple devices interlinked together via the network 150, wherein the devices may be distributed over a large geographic area and performing different functions or similar functions. For instance, two or more servers 110 may be implemented to work as a single server 110 performing the same tasks. Alternatively, one server 110 may perform the functions of multiple servers 110. For instance, a single server 110 may perform the tasks of a web server and an indexing server 110. Additionally, it is understood that multiple servers 110 may be used to operably connect the processor 220 to the database 115 and/or other content repositories. The processor 220 may be operably connected to the server 110 via wired or wireless connection. Types of servers 110 that may be used by the system 400 include, but are not limited to, search servers, document indexing servers, and web servers, or any combination thereof.

Search servers may include one or more computing entities 200 designed to implement a search engine, such as a documents/records search engine, general webpage search engine, etc. Search servers may, for instance, include one or more web servers designed to receive search queries and/or inputs from users 405, search one or more databases 115 in response to the search queries and/or inputs, and provide documents or information, relevant to the search queries and/or inputs, to users 405. In some implementations, search servers may include a web search server that may provide webpages to users 405, wherein a provided webpage may include a reference to a web server at which the desired information and/or links are located. The references to the web server at which the desired information is located may be included in a frame and/or text box, or as a link to the desired information/document. Document indexing servers may include one or more devices designed to index documents available through networks 150. Document indexing servers may access other servers 110, such as web servers that host content, to index the content. In some implementations, document indexing servers may index documents/records stored by other servers 110 connected to the network 150. Document indexing servers may, for instance, store and index content, information, and documents relating to user accounts and user-generated content. Web servers may include servers 110 that provide webpages to clients 105. For instance, the webpages may be HTML-based webpages. A web server may host one or more websites. As used herein, a website may refer to a collection of related webpages. Frequently, a website may be associated with a single domain name, although some websites may potentially encompass more than one domain name. The concepts described herein may be applied on a per-website basis. Alternatively, in some implementations, the concepts described herein may be applied on a per-webpage basis.

As used herein, a database 115 refers to a set of related data and the way it is organized. Access to this data is usually provided by a database management system (DBMS) consisting of an integrated set of computer software that allows users 405 to interact with one or more databases 115 and provides access to all of the data contained in the database 115. The DBMS provides various functions that allow entry, storage and retrieval of large quantities of information and provides ways to manage how that information is organized. Because of the close relationship between the database 115 and the DBMS, as used herein, the term database 115 refers to both a database 115 and DBMS.

Figure 2:
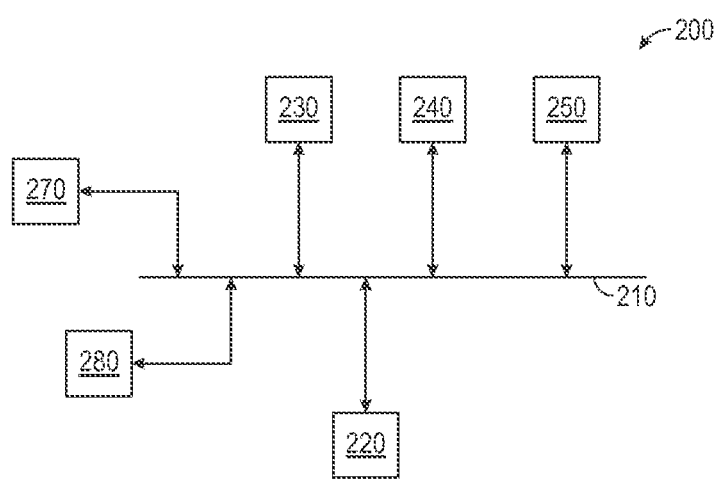
FIG. 2 illustrates a system embodying features consistent with the principles of the present disclosure.

FIG. 2 is an exemplary diagram of a client 105, server 110, and/or or database 115 (hereinafter collectively referred to as "computing entity 200"), which may correspond to one or more of the clients 105, servers 110, and databases 115 according to an implementation consistent with the principles of the invention as described herein. The computing entity 200 may comprise a bus 210, a processor 220, memory 304, a storage device 250, a peripheral device 270, and a communication interface 280 (such as wired or wireless communication device). The bus 210 may be defined as one or more conductors that permit communication among the components of the computing entity 200. The processor 220 may be defined as logic circuitry that responds to and processes the basic instructions that drive the computing entity 200. Memory 304 may be defined as the integrated circuitry that stores information for immediate use in a computing entity 200. A peripheral device 270 may be defined as any hardware used by a user 405 and/or the computing entity 200 to facilitate communicate between the two. A storage device 250 may be defined as a device used to provide mass storage to a computing entity 200. A communication interface 280 may be defined as any transceiver-like device that enables the computing entity 200 to communicate with other devices and/or computing entities 200.

The bus 210 may comprise a high-speed interface 308 and/or a low-speed interface 312 that connects the various components together in a way such they may communicate with one another. A high-speed interface 308 manages bandwidth-intensive operations for computing device 300, while a low-speed interface 312 manages lower bandwidth-intensive operations. In some preferred embodiments, the high-speed interface 308 of a bus 210 may be coupled to the memory 304, display 316, and to high-speed expansion ports 310, which may accept various expansion cards such as a graphics processing unit (GPU). In other preferred embodiments, the low-speed interface 312 of a bus 210 may be coupled to a storage device 250 and low-speed expansion ports 314. The low-speed expansion ports 314 may include various communication ports, such as USB, Bluetooth, Ethernet, wireless Ethernet, etc. Additionally, the low-speed expansion ports 314 may be coupled to one or more peripheral devices 270, such as a keyboard, pointing device, scanner, and/or a networking device, wherein the low-speed expansion ports 314 facilitate the transfer of input data from the peripheral devices 270 to the processor 220 via the low-speed interface 312.

The processor 220 may comprise any type of conventional processor or microprocessor that interprets and executes computer readable instructions. The processor 220 is configured to perform the operations disclosed herein based on instructions stored within the system 400. The processor 220 may process instructions for execution within the computing entity 200, including instructions stored in memory 304 or on a storage device 250, to display graphical information for a graphical user interface (GUI) on an external peripheral device 270, such as a display 316. The processor 220 may provide for coordination of the other components of a computing entity 200, such as control of user interfaces 411A, 411B, applications run by a computing entity 200, and wireless communication by a communication interface 280 of the computing entity 200. The processor 220 may be any processor or microprocessor suitable for executing instructions. In some embodiments, the processor 220 may have a memory device therein or coupled thereto suitable for storing the data, content, or other information or material disclosed herein. In some instances, the processor 220 may be a component of a larger computing entity 200. A computing entity 200 that may house the processor 220 therein may include, but are not limited to, laptops, desktops, workstations, personal digital assistants, servers 110, mainframes, cellular telephones, tablet computers, smart televisions, streaming devices, smart watches, or any other similar device. Accordingly, the inventive subject matter disclosed herein, in full or in part, may be implemented or utilized in devices including, but are not limited to, laptops, desktops, workstations, personal digital assistants, servers 110, mainframes, cellular telephones, tablet computers, smart televisions, streaming devices, or any other similar device.

Memory 304 stores information within the computing device 300. In some preferred embodiments, memory 304 may include one or more volatile memory units. In another preferred embodiment, memory 304 may include one or more non-volatile memory units. Memory 304 may also include another form of computer-readable medium, such as a magnetic, solid state, or optical disk. For instance, a portion of a magnetic hard drive may be partitioned as a dynamic scratch space to allow for temporary storage of information that may be used by the processor 220 when faster types of memory, such as random-access memory (RAM), are in high demand. A computer-readable medium may refer to a non-transitory computer-readable memory device. A memory device may refer to storage space within a single storage device 250 or spread across multiple storage devices 250. The memory 304 may comprise main memory 230 and/or read only memory (ROM) 240. In a preferred embodiment, the main memory 230 may comprise RAM or another type of dynamic storage device 250 that stores information and instructions for execution by the processor 220. ROM 240 may comprise a conventional ROM device or another type of static storage device 250 that stores static information and instructions for use by processor 220. The storage device 250 may comprise a magnetic and/or optical recording medium and its corresponding drive.

As mentioned earlier, a peripheral device 270 is a device that facilitates communication between a user 405 and the processor 220. The peripheral device 270 may include, but is not limited to, an input device and/or an output device. As used herein, an input device may be defined as a device that allows a user 405 to input data and instructions that is then converted into a pattern of electrical signals in binary code that are comprehensible to a computing entity 200. An input device of the peripheral device 270 may include one or more conventional devices that permit a user 405 to input information into the computing entity 200, such as a controller, scanner, phone, camera, scanning device, keyboard, a mouse, a pen, voice recognition and/or biometric mechanisms, etc. As used herein, an output device may be defined as a device that translates the electronic signals received from a computing entity 200 into a form intelligible to the user 405. An output device of the peripheral device 270 may include one or more conventional devices that output information to a user 405, including a display 316, a printer, a speaker, an alarm, a projector, etc. Additionally, storage devices 250, such as CD-ROM drives, and other computing entities 200 may act as a peripheral device 270 that may act independently from the operably connected computing entity 200. For instance, a streaming device may transfer data to a smartphone, wherein the smartphone may use that data in a manner separate from the streaming device.

The storage device 250 is capable of providing the computing entity 200 mass storage. In some embodiments, the storage device 250 may comprise a computer-readable medium such as the memory 304, storage device 250, or memory 304 on the processor 220. A computer-readable medium may be defined as one or more physical or logical memory devices and/or carrier waves. Devices that may act as a computer readable medium include, but are not limited to, a hard disk device, optical disk device, tape device, flash memory or other similar solid-state memory device, or an array of devices, including devices in a storage area network or other configurations. Examples of computer-readable mediums include, but are not limited to, magnetic media such as hard disks, floppy disks, and magnetic tape; optical media such as CD ROM discs and DVDs; magneto-optical media such as optical discs; and hardware devices that are specially configured to store and perform programming instructions, such as ROM 240, RAM, flash memory, and the like.

In an embodiment, a computer program may be tangibly embodied in the storage device 250. The computer program may contain instructions that, when executed by the processor 220, performs one or more steps that comprise a method, such as those methods described herein. The instructions within a computer program may be carried to the processor 220 via the bus 210. Alternatively, the computer program may be carried to a computer-readable medium, wherein the information may then be accessed from the computer-readable medium by the processor 220 via the bus 210 as needed. In a preferred embodiment, the software instructions may be read into memory 304 from another computer-readable medium, such as data storage device 250, or from another device via the communication interface 280. Alternatively, hardwired circuitry may be used in place of or in combination with software instructions to implement processes consistent with the principles as described herein. Thus, implementations consistent with the invention as described herein are not limited to any specific combination of hardware circuitry and software.

Figure 3:
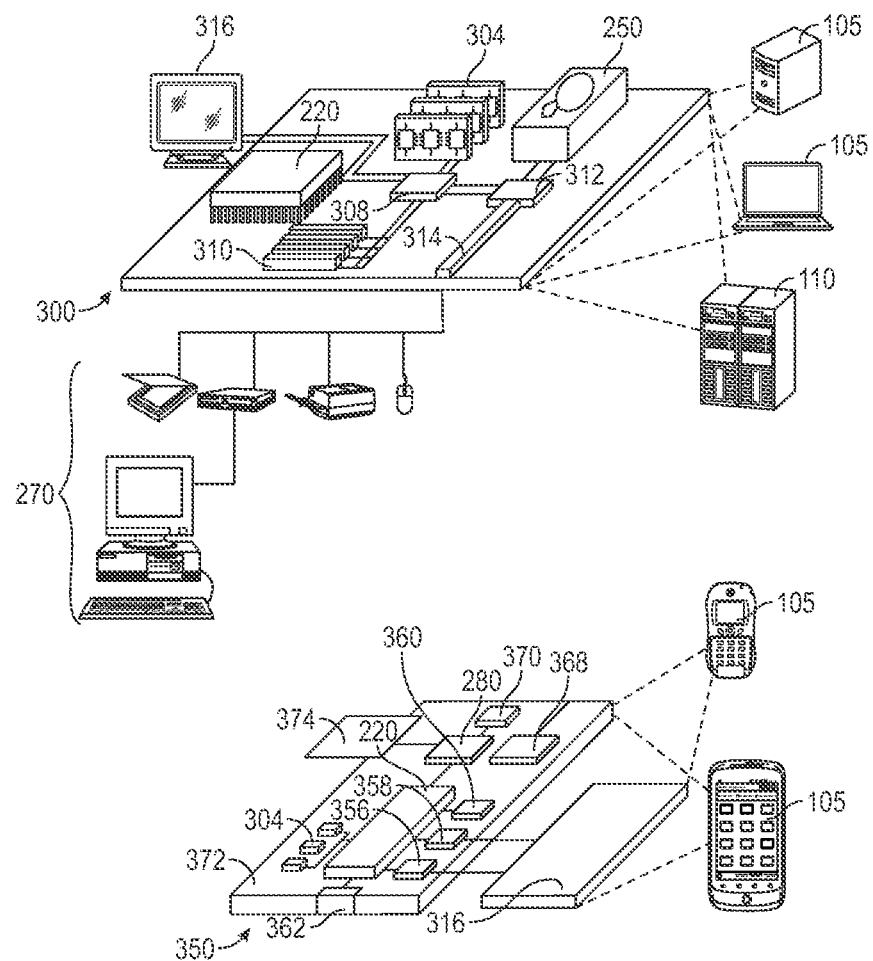
FIG. 3 illustrates a system embodying features consistent with the principles of the present disclosure.

FIG. 3 depicts exemplary computing entities 200 in the form of a computing device 300 and mobile computing device 350, which may be used to carry out the various embodiments of the invention as described herein. A computing device 300 is intended to represent various forms of digital computers, such as laptops, desktops, workstations, servers 110, databases 115, mainframes, and other appropriate computers. A mobile computing device 350 is intended to represent various forms of mobile devices, such as scanners, scanning devices, personal digital assistants, cellular telephones, smart phones, tablet computers, and other similar devices. The various components depicted in FIG. 3, as well as their connections, relationships, and functions are meant to be examples only, and are not meant to limit the implementations of the invention as described herein. The computing device 300 may be implemented in a number of different forms, as shown in FIGS. 1 and 3. For instance, a computing device 300 may be implemented as a server 110 or in a group of servers 110. Computing devices 300 may also be implemented as part of a rack server system. In addition, a computing device 300 may be implemented as a personal computer, such as a desktop computer or laptop computer. Alternatively, components from a computing device 300 may be combined with other components in a mobile device, thus creating a mobile computing device 350. Each mobile computing device 350 may contain one or more computing devices 300 and mobile devices, and an entire system may be made up of multiple computing devices 300 and mobile devices communicating with each other as depicted by the mobile computing device 350 in FIG. 3. The computing entities 200 consistent with the principles of the invention as disclosed herein may perform certain receiving, communicating, generating, output providing, correlating, and storing operations as needed to perform the various methods as described in greater detail below.

In the embodiment depicted in FIG. 3, a computing device 300 may include a processor 220, memory 304 a storage device 250, high-speed expansion ports 310, low-speed expansion ports 314, and bus 210 operably connecting the processor 220, memory 304, storage device 250, high-speed expansion ports 310, and low-speed expansion ports 314. In one preferred embodiment, the bus 210 may comprise a high-speed interface 308 connecting the processor 220 to the memory 304 and high-speed expansion ports 310 as well as a low-speed interface 312 connecting to the low-speed expansion ports 314 and the storage device 250. Because each of the components are interconnected using the bus 210, they may be mounted on a common motherboard as depicted in FIG. 3 or in other manners as appropriate. The processor 220 may process instructions for execution within the computing device 300, including instructions stored in memory 304 or on the storage device 250. Processing these instructions may cause the computing device 300 to display graphical information for a GUI on an output device, such as a display 316 coupled to the high-speed interface 308. In other implementations, multiple processors and/or multiple buses may be used, as appropriate, along with multiple memory units and/or multiple types of memory. Additionally, multiple computing devices may be connected, wherein each device provides portions of the necessary operations.

A mobile computing device 350 may include a processor 220, memory 304 a peripheral device 270 (such as a display 316, a communication interface 280, and a transceiver 368, among other components). A mobile computing device 350 may also be provided with a storage device 250, such as a micro-drive or other previously mentioned storage device 250, to provide additional storage. Preferably, each of the components of the mobile computing device 350 are interconnected using a bus 210, which may allow several of the components of the mobile computing device 350 to be mounted on a common motherboard as depicted in FIG. 3 or in other manners as appropriate. In some implementations, a computer program may be tangibly embodied in an information carrier. The computer program may contain instructions that, when executed by the processor 220, perform one or more methods, such as those described herein. The information carrier is preferably a computer-readable medium, such as memory, expansion memory 374, or memory 304 on the processor 220 such as ROM 240, that may be received via the transceiver or external interface 362. The mobile computing device 350 may be implemented in a number of different forms, as shown in FIG. 3. For instance, a mobile computing device 350 may be implemented as a cellular telephone, part of a smart phone, personal digital assistant, or other similar mobile device.

The processor 220 may execute instructions within the mobile computing device 350, including instructions stored in the memory 304 and/or storage device 250. The processor 220 may be implemented as a chipset of chips that may include separate and multiple analog and/or digital processors. The processor 220 may provide for coordination of the other components of the mobile computing device 350, such as control of the user interfaces 411A, 411B, applications run by the mobile computing device 350, and wireless communication by the mobile computing device 350. The processor 220 of the mobile computing device 350 may communicate with a user 405 through the control interface 358 coupled to a peripheral device 270 and the display interface 356 coupled to a display 316. The display 316 of the mobile computing device 350 may include, but is not limited to, Liquid Crystal Display (LCD), Light Emitting Diode (LED) display, Organic Light Emitting Diode (OLED) display, and Plasma Display Panel (PDP), holographic displays, augmented reality displays, virtual reality displays, or any combination thereof. The display interface 356 may include appropriate circuitry for causing the display 316 to present graphical and other information to a user 405. The control interface 358 may receive commands from a user 405 via a peripheral device 270 and convert the commands into a computer readable signal for the processor 220. In addition, an external interface 362 may be provided in communication with processor 220, which may enable near area communication of the mobile computing device 350 with other devices. The external interface 362 may provide for wired communications in some implementations or wireless communication in other implementations. In a preferred embodiment, multiple interfaces may be used in a single mobile computing device 350 as is depicted in FIG. 3.

Memory 304 stores information within the mobile computing device 350. Devices that may act as memory 304 for the mobile computing device 350 include, but are not limited to computer-readable media, volatile memory, and non-volatile memory. Expansion memory 374 may also be provided and connected to the mobile computing device 350 through an expansion interface 372, which may include a Single In-Line Memory Module (SIM) card interface or micro secure digital (Micro-SD) card interface. Expansion memory 374 may include, but is not limited to, various types of flash memory and non-volatile random-access memory (NVRAM). Such expansion memory 374 may provide extra storage space for the mobile computing device 350. In addition, expansion memory 374 may store computer programs or other information that may be used by the mobile computing device 350. For instance, expansion memory 374 may have instructions stored thereon that, when carried out by the processor 220, cause the mobile computing device 350 perform the methods described herein. Further, expansion memory 374 may have secure information stored thereon; therefore, expansion memory 374 may be provided as a security module for a mobile computing device 350, wherein the security module may be programmed with instructions that permit secure use of a mobile computing device 350. In addition, expansion memory 374 having secure applications and secure information stored thereon may allow a user 405 to place identifying information on the expansion memory 374 via the mobile computing device 350 in a non-hackable manner.

A mobile computing device 350 may communicate wirelessly through the communication interface 280, which may include digital signal processing circuitry where necessary. The communication interface 280 may provide for communications under various modes or protocols, including, but not limited to, Global System Mobile Communication (GSM), Short Message Services (SMS), Enterprise Messaging System (EMS), Multimedia Messaging Service (MMS), Code Division Multiple Access (CDMA), Time Division Multiple Access (TDMA), Personal Digital Cellular (PDC), Wideband Code Division Multiple Access (WCDMA), IMT Multi-Carrier (CDMAX 0), and General Packet Radio Service (GPRS), or any combination thereof. Such communication may occur, for example, through a transceiver 368. Short-range communication may occur, such as using a Bluetooth, WIFI, or other such transceiver 368. In addition, a Global Positioning System (GPS) receiver module 370 may provide additional navigation- and location-related wireless data to the mobile computing device 350, which may be used as appropriate by applications running on the mobile computing device 350. Alternatively, the mobile computing device 350 may communicate audibly using an audio codec 360, which may receive spoken information from a user 405 and covert the received spoken information into a digital form that may be processed by the processor 220. The audio codec 360 may likewise generate audible sound for a user 405, such as through a speaker, e.g., in a handset of mobile computing device 350. Such sound may include sound from voice telephone calls, recorded sound such as voice messages, music files, etc. Sound may also include sound generated by applications operating on the mobile computing device 350.

The power supply may be any source of power that provides the system 400 with electricity. In a preferred embodiment, the primary power source of the system is a stationary power source, such as a standard wall outlet. In one preferred embodiment, the system 400 may comprise of multiple power supplies that may provide power to the system 400 in different circumstances. For instance, the system 400 may be connected to a backup battery system, which may provide power to the system 400 when it's primary power source cannot provide power and so long as the batteries of the backup battery system are charged. In this way, the system 400 may receive power even in conditions in which a medical facility may lose power, allowing patients 405B and healthcare professionals 405A to review patient data 430B together even in less hospitable environments.

Figure 4:
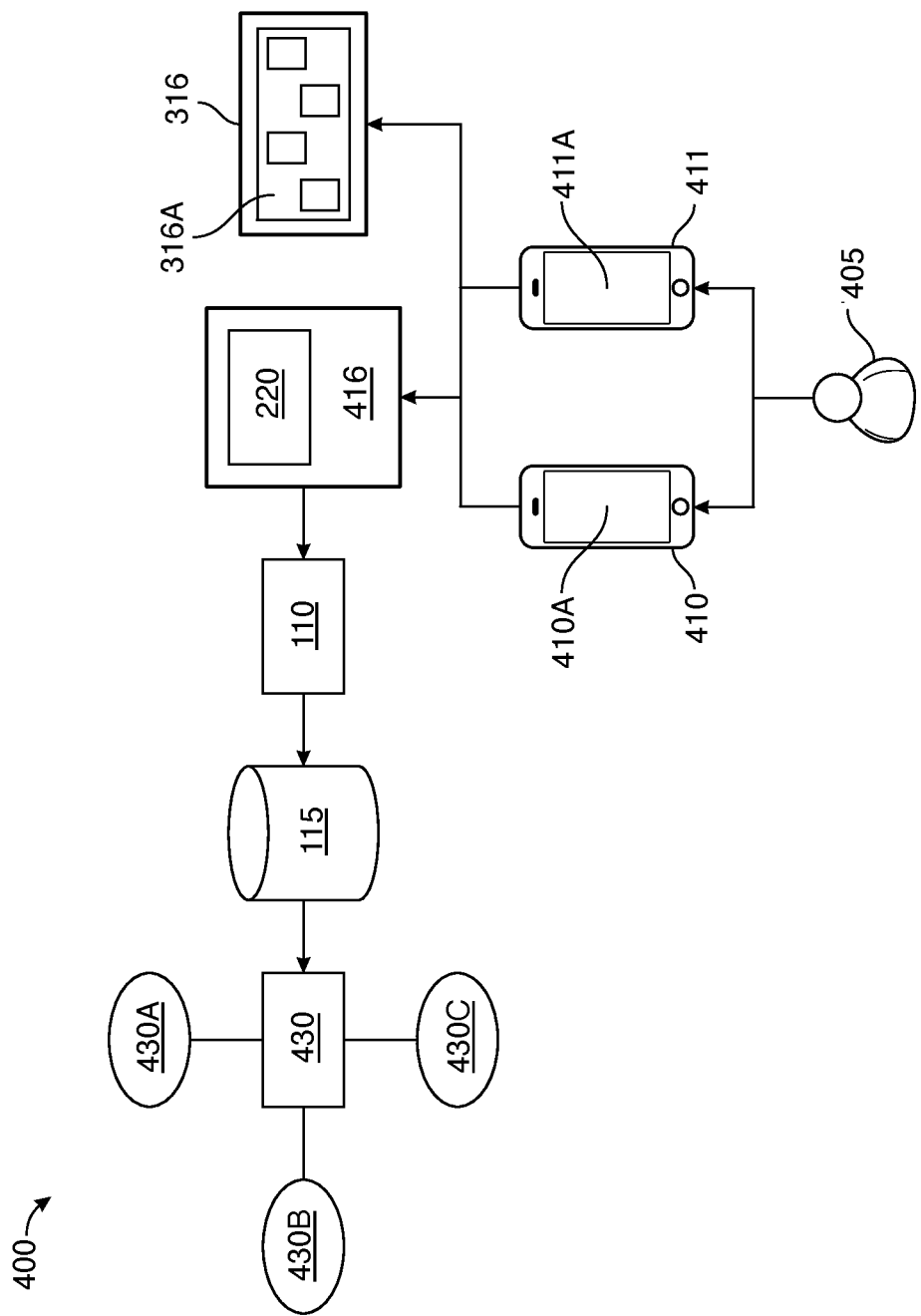
FIG. 4 illustrates a system for managing the transfer of data between displays and computing devices.
Figure 5:
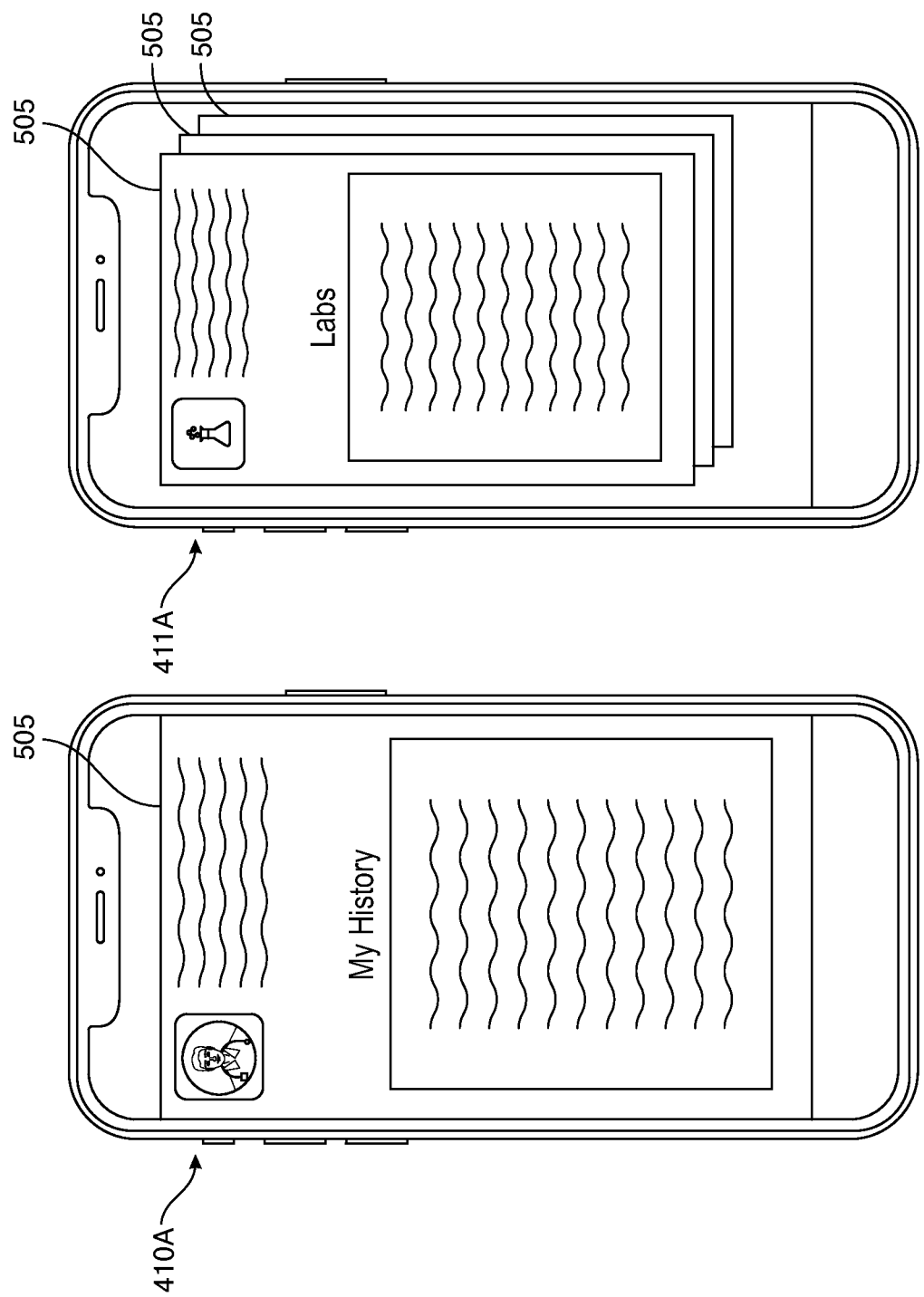
FIG. 5 illustrates user interfaces having application windows that may be used to manage what is presented within the display user interfaces.
Figure 6:
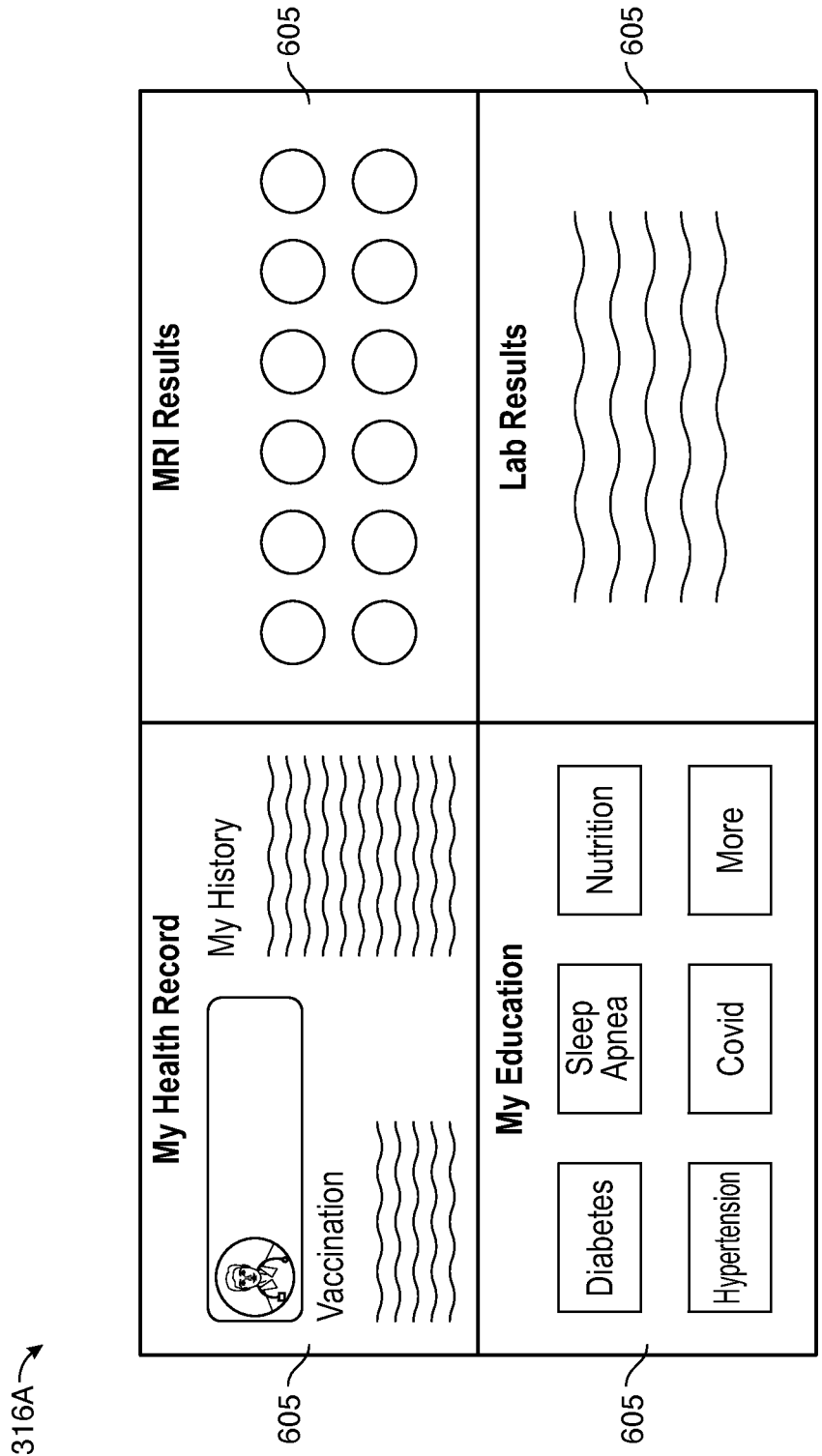
FIG. 6 illustrates a display user interface comprising a plurality of display windows arranged to present data within the selected application windows.
Figure 7:
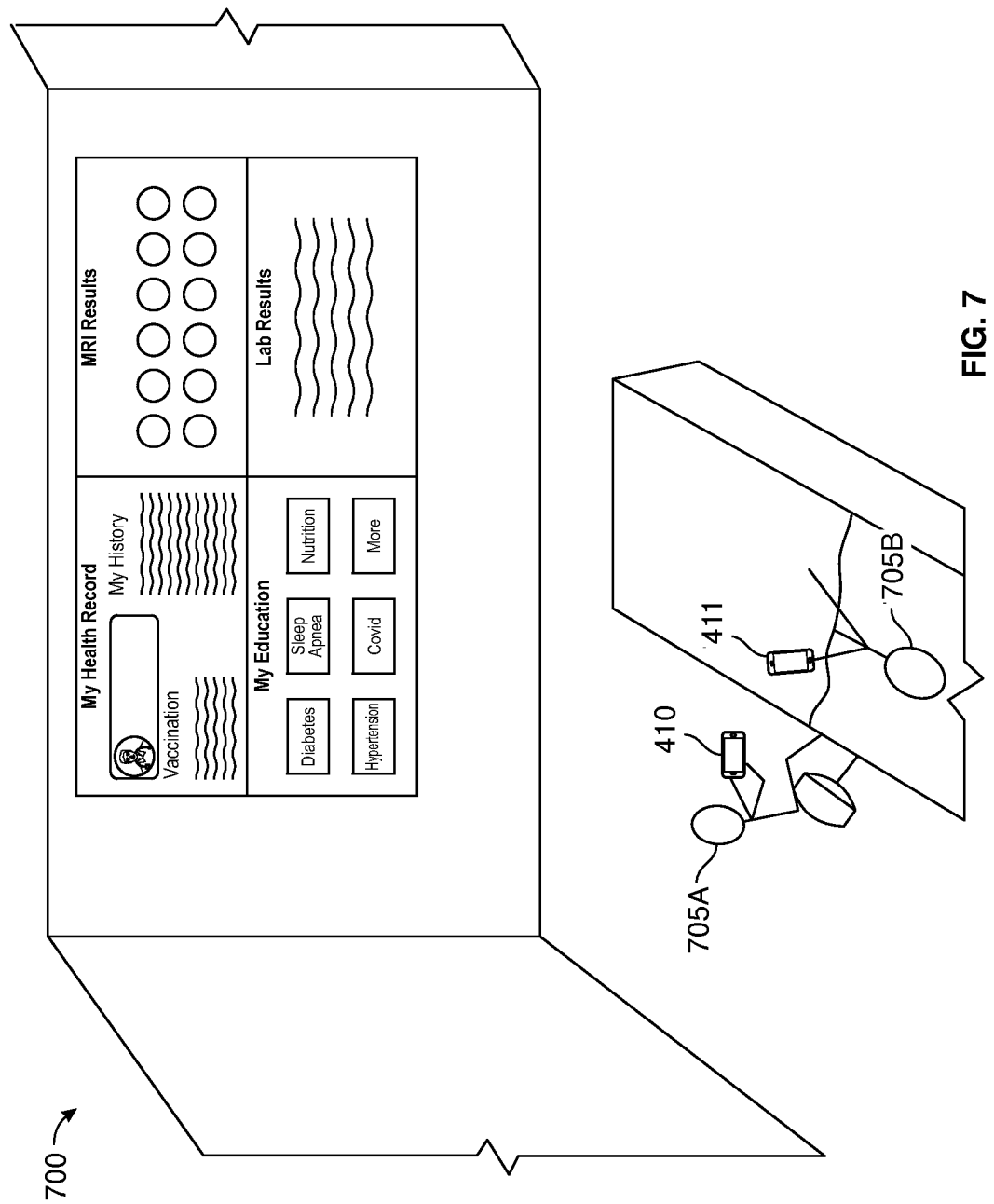
FIG. 7 illustrates a system embodying features consistent with the principles of the present disclosure being used within an environment.
Figure 8:
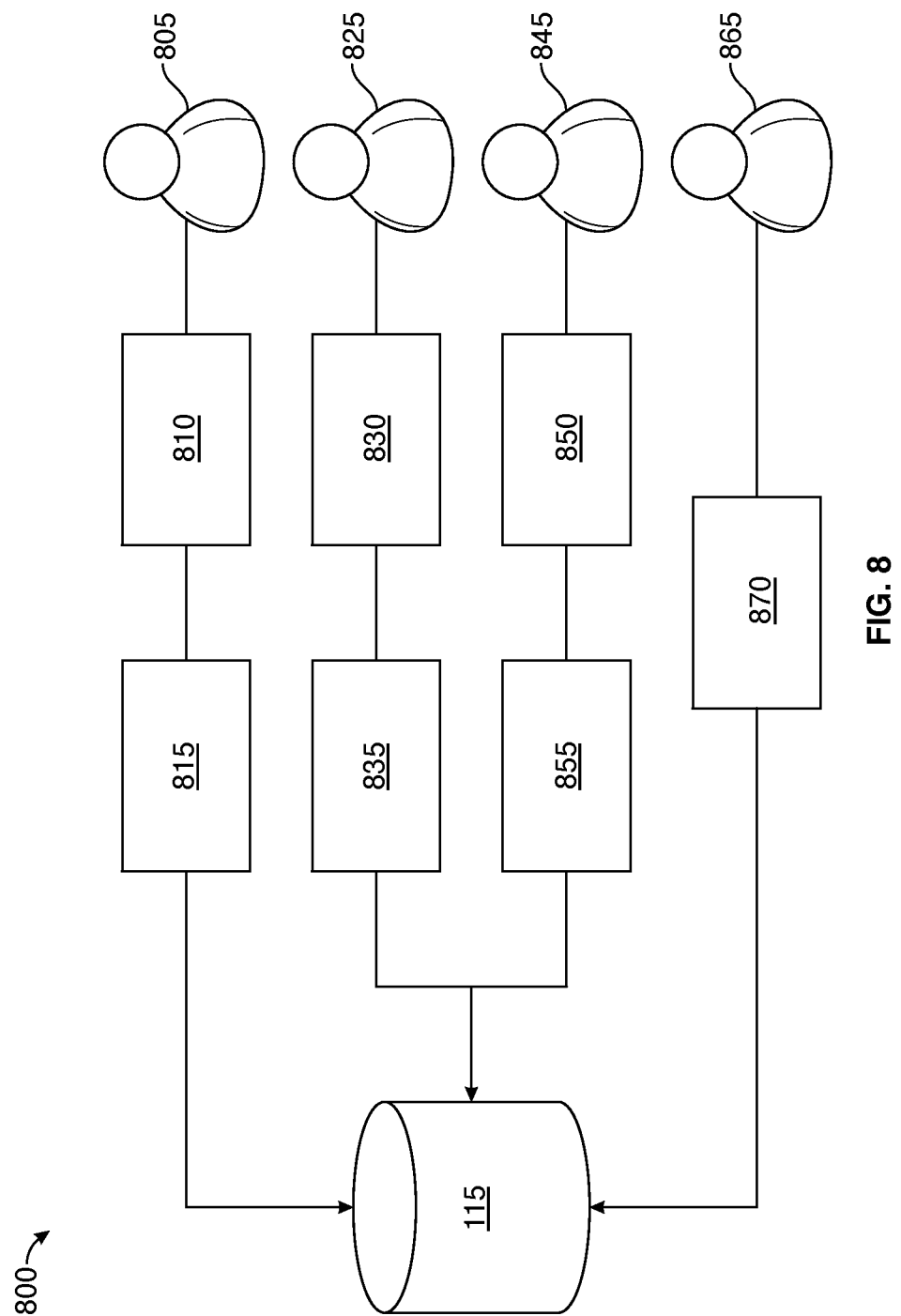
FIG. 8 is a diagram illustrating the manner in which individual access to data may be granted or limited based on user roles and administrator roles.
Figure 9:
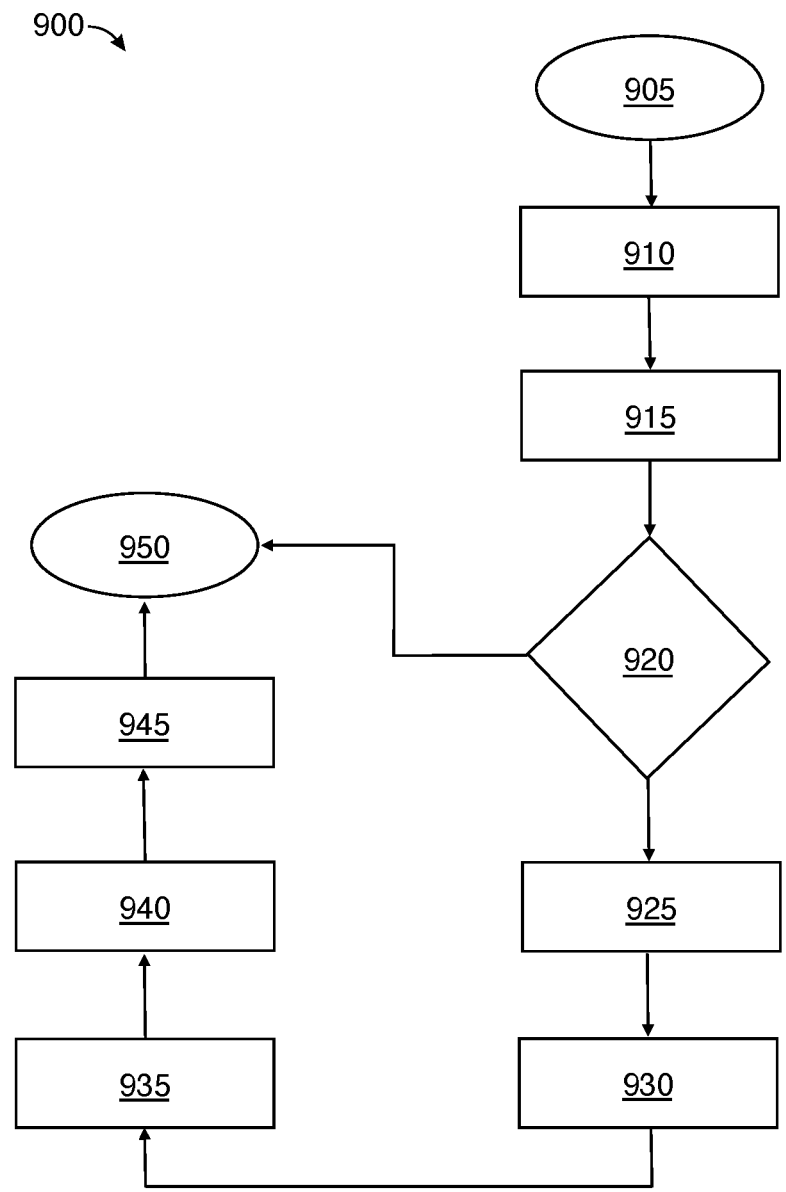
FIG. 9 is a flow chart illustrating certain method steps of a method embodying features consistent with the principles of the present disclosure.
Figure 10:
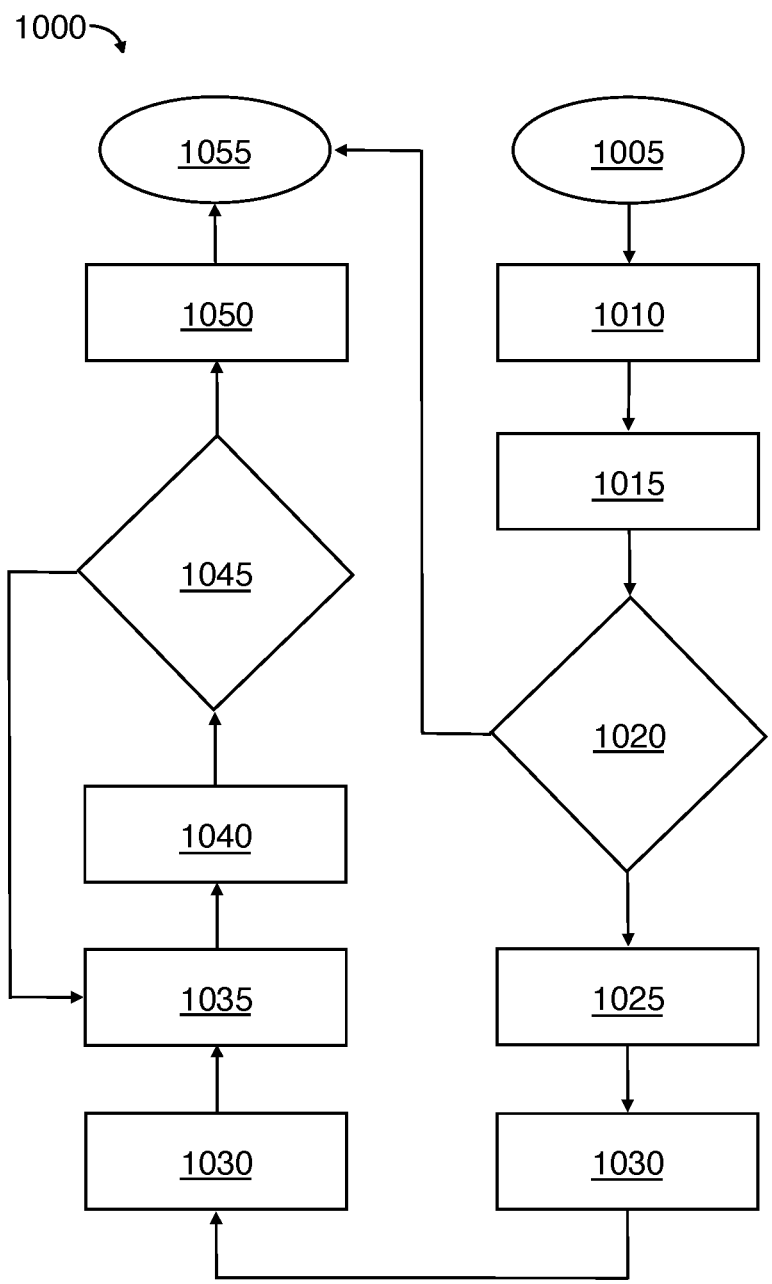
FIG. 10 is a flow chart illustrating certain method steps of a method embodying features consistent with the principles of the present disclosure.
Figure 11:
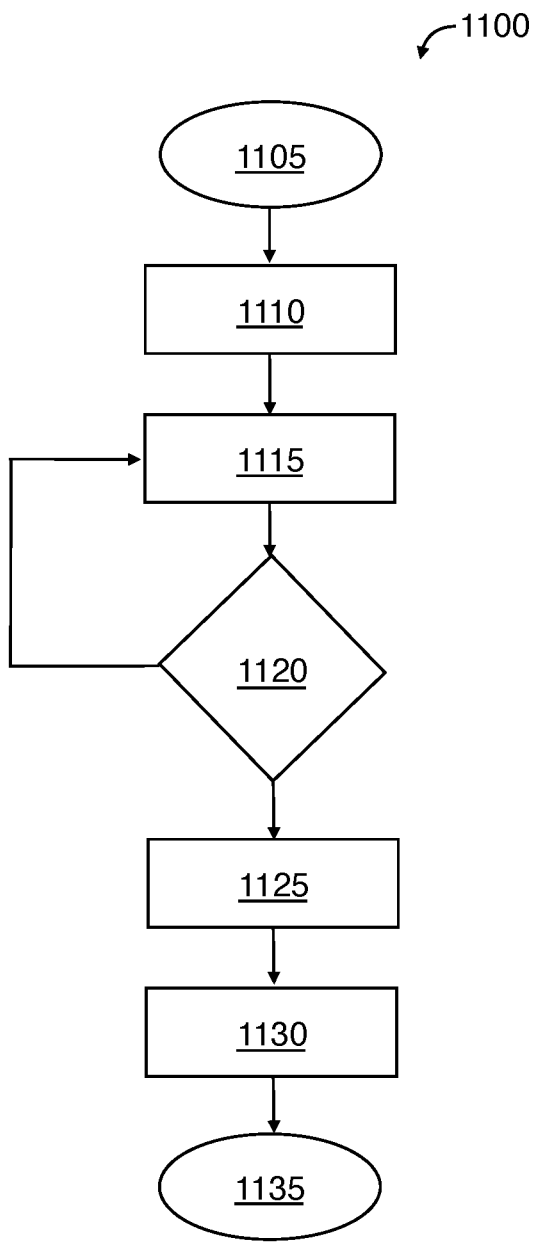
FIG. 11 is a flow chart illustrating certain method steps of a method embodying features consistent with the principles of the present disclosure.

FIGS. 4-11 illustrate embodiments of a system 400 and methods for securely displaying patient data 430B within a plurality of display windows 605 of a display user interface 316A of a display 316 while reducing the amount of data transferred between the various computing entities. FIG. 4 illustrates a preferred embodiment of the system 400 having a first computing device 410 and second computing device 411 operably connected to a display 316. FIG. 5 illustrates an example first user interface 410A of the first computing device 410 and a second user interface 411A of a second computing device 411, wherein a display 316 operably connected to said first computing device 410 and second computing device 411 may receive image data 430C from said first user interface 410A of said first computing device 410 and said second user interface 411A from said second computing device 411, wherein said image data 430C contains patient data 430B. FIG. 6 illustrates an example display user interface 316A of the display 316, wherein a control board operably connected to said display 316 may receive image data 430C from said first computing device 410 and said second computing device 411 and present it within said display user interface 316A. FIG. 7 illustrates an environmental view of the system 400 being used by a user 405 within a hospital environment 700. FIG. 8 illustrates permission levels 800 that may be utilized by the system 400 for controlling access to user content 815, 835, 855 such as user data 430A, patient data 430B, and image data 430C. FIGS. 9-11 illustrate methods that may be carried out by the system 400. It is understood that the various method steps associated with the methods of the present disclosure may be carried out as operations by the system 400 shown in FIG. 4.

The system 400 generally comprises a first computing device 410 having a first user interface 410A, second computing device 411 having a second user interface 411A, processor 220 operably connected to said first computing device 410 and said second computing device 411, display 316 operably connected to said processor 220, and non-transitory computer-readable medium 416 coupled to said processor 220 and having instructions stored thereon. In one preferred embodiment, a database 115 may be operably connected to the processor 220 and the various data of the system 400 may be stored therein, including, but not limited to, user data 430A, patient data 430B, and image data 430C. In a preferred embodiment, the various data of the system 400 transferred between the computing entities is encrypted. Other embodiments may further comprise a server 110 operably connected to the processor 220 and database 115, facilitating the transfer of data therebetween. In some preferred embodiments, a display user interface 316A of the display 316 may comprise a plurality of display windows 605 configured to present image data 430C therein, wherein a control board of the display 316 may be configured to receive said image data 430C from said first computing device 410 and said second computing device 411. In yet another preferred embodiment, a wireless communication interface may allow the various pieces of the system 400 to receive and transmit image data 430C therebetween. Though computing entities are referred to as first computing device 410, second computing device 411, and display 316 having a control board, one with skill in the art will recognize instances in which said computing entities may be used interchangeably without departing from the inventive subject matter described herein.

As previously mentioned, the processor 220 is configured to perform the operations disclosed herein based on instructions stored within the system 400. In an embodiment, the programming instructions responsible for the operations carried out by the processor 220 are stored on a non-transitory computer-readable medium ("CRM") 416, which may be coupled to the server 110, as illustrated in FIG. 4. Alternatively, the programming instructions may be stored or included within the processor 220. Examples of non-transitory computer-readable mediums 416 include, but are not limited to, magnetic media such as hard disks, floppy disks, and magnetic tape; optical media such as CD ROM discs and DVDs; magneto-optical media such as optical discs; and hardware devices that are specifically configured to store and perform programming instructions, such as read-only memory (ROM), random access memory (RAM), flash memory, and the like. In some embodiments, the programming instructions may be stored as modules within the non-transitory computer-readable medium 416.

Data within the system 400 may be stored in various profiles. In a preferred embodiment, the system 400 comprises user data 430A, patient data 430B, and image data 430C that may be stored in user profiles 430. A user profile 430 may be defined as a profile containing data about a particular user 405. As used herein, user data 430A may be defined as personal information of a user 405 that helps the system 400 identify the user 405. Types of data that may be used by the system 400 as user data 430A includes, but is not limited to, a user's name, username, social security number, phone number, gender, age, or any combination thereof. As used herein, patient data 430B is data related to a patient's 705B 405B medical record, which may usually be found within an Electronic Health Record (EHR). Types of data that may be used by the system 400 as patient data 430B includes, but is not limited to, encounter notes, problems lists, lab/image reports, orders, medications, guidelines, assessments, interventions, pathological reports, or any combination thereof. Image data 430C may be defined as data containing a visual representation of a particular user's 405 patient data 430B as displayed in at least one of the first user interface 410A and second user interface 411A. User data 430A, patient data 430B, and image data 430C in combination with permission levels 800 is used by the system 400 to assist in presenting patient data 430B to users within the display user interface 316A. A user 405 is preferably associated with a particular user profile 430 based on a username. However, it is understood that a user 405 may be associated with a user profile 430 using a variety of methods without departing from the inventive subject matter herein.

As illustrated in FIG. 4, the system 400 may comprise a database 115 operably connected to the processor 220. The database 115 may be operably connected to the processor 220 via wired or wireless connection. In a preferred embodiment, the database 115 is configured to store user data 430A, patient data 430B, and image data 430C therein. Alternatively, the user data 430A, patient data 430B, and image data 430C may be stored on the non-transitory computer-readable medium 416. The database 115 may be a relational database such that the user data 430A, patient data 430B, and image data 430C associated with each user profile 430 within the plurality of user profiles may be stored, at least in part, in one or more tables. Alternatively, the database 115 may be an object database such that user data 430A, patient data 430B, and image data 430C associated with each user profile 430 within the plurality of user profiles may be stored, at least in part, as objects. In some instances, the database 115 may comprise a relational and/or object database and a server 110 dedicated solely to managing the user data 430A, patient data 430B, and image data 430C in the manners disclosed herein.

The computing entities themselves may further comprise a display 316. A display 316 may be defined as an output device that communicates data that may include, but is not limited to, visual, auditory, cutaneous, kinesthetic, olfactory, and gustatory, or any combination thereof. Information presented via a display 316 may be referred to as a soft copy of the information because the information exists electronically and is presented for a temporary period of time. Information stored on the non-transitory computer-readable medium 416 may be referred to as the hard copy of the information. For instance, a display 316 may present a soft copy of a visual representation of patient data 430B via a liquid crystal display (LCD), wherein the hard copy of the patient data 430B may be stored on a local hard drive. For instance, a display 316 may present a soft copy of audio information via a speaker, wherein the hard copy of the audio information is stored in memory of a mobile computing entity 200. For instance, a display 316 may present a soft copy of user data 430A via a hologram, wherein the hard copy of the user data 430A is stored within a database 115. Displays may include, but are not limited to, cathode ray tube monitors, LCD monitors, light emitting diode (LED) monitors, gas plasma monitors, screen readers, speech synthesizers, holographic displays, speakers, and scent generating devices, or any combination thereof, but is not limited to these devices.

A user 405 preferably accesses the various data of the system 400 by inputting commands within a user interface of a computing entity 200 that allows the user 405 to access to said data. In a preferred embodiment, as illustrated in FIGS. 7 and 8, a user 405 may access data of the system 400 by using a first user interface 410A of a first computing device 410 or a second user interface of a second computing device 411 to login to a user profile 430 having permissions 800 that allows said user 405 to access user data 430A, patient data 430B, and image data 430C of said user profile 430. After logging into said user profile 430 via one of said first user interface 410A and second user interface 411A, the user may connect the computing entity 200 with the display so that the user interface may instruct the processor 220 in way that causes the processor 220 to facilitate the transfer of image data 430C from the computing entity 200 to the display 316. Some preferred embodiments may require a security method to connect the computing entity 200 to the display 316. For instance, the system 400 may require a user 405 to scan a barcode of the display 316 before granting access to said display 316. Once connected, the user interface may cause the processor 220 to transmit image data 430C to the display 316, which may subsequently be presented via the display user interface 316A.

Types of devices that may act as the communication interface include, but are not limited, to near field communication (NFC), Bluetooth, infrared (IR), radio-frequency communication (RFC), radio-frequency identification (RFID), and ANT+, or any combination thereof. In an embodiment, communication interfaces may broadcast signals of more than one type. For instance, a communication interface comprising an IR transmitter and RFID transmitter may broadcast IR signals and RFID signals. Alternatively, a communication interface may broadcast signals of only one type of signal. For instance, ID badges may be fitted with communication interface that broadcast only NFC signals containing unique IDs that computing entities equipped with NFC receivers must receive before being activated by a user 405.

As previously mentioned, some preferred embodiments of the display 316 may further comprise a control board. The control board comprises at least one circuit and microchip. In another preferred embodiment, the control board may further comprise a wireless communication interface, which may allow the control board to receive instructions from an input device controlled by a user 405. In a preferred embodiment, the control board may control the plurality of display windows 605 of the display user interface 316A and the image data 430C displayed therein. The microchip of the control board comprises a microprocessor 220 and memory. In another preferred embodiment, the microchip may further comprise a wireless communication interface in the form of an antenna. The microprocessor 220 may be defined as a multipurpose, clock driven, register based, digital-integrated circuit which accepts binary data as input, processes it according to instructions stored in its memory, and provides results as output. In a preferred embodiment, the microprocessor 220 may receive image data 430C from at least one of a first computing device 410 and second computing device 411 via the wireless communication interface, wherein the image data 430C comprises both image data 430C and video data. Some preferred embodiments of image data 430C may also include an audio data component. In another preferred embodiment, the microprocessor 220 may receive image data 430C from the communication interface in the form of a live stream. For instance, image data 430C pertaining to a live recording of a patient 705B snoring during a sleep study may include both a video component and an audio component in real time.

As mentioned previously, the system 400 may further comprise a plurality of user interfaces 410A, 411A, 412A. A user interface may be defined as a space where interactions between a user 405 and the system 400 may take place. In an embodiment, the interactions may take place in a way such that a user 405 may control the operations of the system 400. A user interface may include, but is not limited to operating system 400s, command line user interfaces, conversational interfaces, web-based user interfaces, zooming user interfaces, touch screens, task-based user interfaces, touch user interfaces, text-based user interfaces, intelligent user interfaces, brain-computer interfaces (BCIs), and graphical user interfaces, or any combination thereof. The system 400 may present data of the user interface to the user 405 via a display 316 operably connected to the processor 220. A display 316 may be defined as an output device that communicates data that may include, but is not limited to, visual, auditory, cutaneous, kinesthetic, olfactory, and gustatory, or any combination thereof.

As mentioned previously, the control board of the display 316 receives image data 430C from the first computing device 410 and second computing device 411. The user interfaces of the computing entities allow for a user 405 to have a plurality of application windows 505 open thereon, wherein each application window 505 of said plurality of application windows contains a visual representation of a user's 405 patient data 430B. In a preferred embodiment, the user interfaces allow a user 405 to choose which application windows 505 are transmitted to the display 316. The control board may then present said image data 430C via the plurality of display windows 605 of the display user interface 316A. In a preferred embodiment, the user interfaces of the first computing device 410 and second computing device 411 may comprise of active application windows and inactive application windows. Preferably only an active application window of the user interfaces of the first computing device 410 and/or second computing device 411 is sent to the control board of the display 316 as image data 430C in the form of a live stream and/or mirror, wherein an active application window is defined as the application window of the user interface currently being manipulated by a user 405 on their respective computing entity 200. The inactive application windows are presented within the display user interface 316A using the last image data 430C received pertaining to said inactive application window, wherein the inactive application window is defined as an application window of the user interface not currently being manipulated by a user 405 on their respective computing entity 200.

By limiting which application windows 505 of the first user interface 410A and second user interface 411A are mirrored and/or lived streamed, the amount of data transferred between the first computing device 410, second computing device 411, and display 316 can be greatly reduced. For instance, a healthcare professional 705A having a first computing device 410 may wish to share three application windows 505 containing patient data 430B and one application window 505 containing user data 430A with a patient 705B via the display 316. The patient 705B having a second computing device 411 may like to share one application window 505 containing patient data 430B with said healthcare professional 705A via the same display 316. Using the system 400, the healthcare professional 705A and patient 705B may operably connect their respective computing entities to the display 316 and open application windows 505 containing the data that they would like to share. Their computing entities would then convert those visual representations of said data into image data 430C, which their respective computing entities would transmit to the display 316 and the display 316 would then present via the display user interface 316A. In order to minimize the amount of data transferred between the display 316 and the computing entities of the healthcare professional 705A and patient 705B, the system 400 may limit which application windows 505 of the computing entities are mirrored and/or live streamed from the computing entities to the display 316 to only active application windows. This will allow for multiple application windows 505 to be presented within the display user interface 316A without the need for multiple video feeds being transferred between the devices.

The control board may be responsible for managing the presentation of image data 430C of the application windows 505 via the plurality of display windows 605. The layout of the display windows 605 within the display user interface 316A may be manually selected by a user 405 having appropriate permission levels 800. Alternatively, the control board may automatically select a layout of the display user interface 316A, wherein said layout may be determined based on a plurality of variables, including, but not limited to, number of application windows 505 selected, type of data presented, user preferences, patient 705B preferences, user location, patient 705B location, device type, or any combination thereof. For instance, the control board may select a layout of display windows 605 within a display user interface 316A comprising a split screen with three display windows on each half of said split screen, wherein the left half represents selected application windows 505 within the user interface of the healthcare professional's 705A computing entity 200 and the right half represents selected application windows 505 within the user interface of the patient's 705B computing entity 200. Additionally, the topmost display window of each respective half of the split screen may represent an active display window for the healthcare professional 705A and an active display window for the patient 705B.

Alternatively, the control board may manipulate the image data 430C and/or plurality of display windows 605 based on commands received from an input device. In one preferred embodiment, the display user interface 316A may further comprise a control window, which may allow a user 405 to control the layout of the display user interface 316A. For instance, a user 405 may choose a layout of the control window that separates the display user interface 316A into four separate display windows 605 configured to present image data 430C from four separate application windows 505. In another preferred embodiment, the input device may communicate a command to the control board, which the control board uses to manipulate the image data 430C and/or plurality of display windows 605. In an embodiment, an input device having a plurality of keys representing layouts of the display windows 605 may be used to manipulate said display user interface 316A. A control board of the input device may be operably connected to the plurality of keys in a way such that manipulation of a key by a user 405 causes the control board to execute a function that causes said input device to send a command to the control board of the display 316 that causes said display 316 to alter the layout of the display user interface 316A, wherein the function executed by the control board of the input device depends on the key selected. Indicia of the keys may represent which layout will be commanded based on the function executed. The input device may be connected to the system 400 via a wired or wireless connection.

In some preferred embodiments, the display 316 may communicate with a user's 405 computing entity 200 to limit the functionality of the user interface of said computing entity 200. In one preferred embodiment, settings of the display 316 may limit how many application windows 505 may be selected for presentation within the display user interface 316A. For instance, a display 316 may be configured such that the number of display windows 505 that may be used by the display 316 to present image data 430C is limited to five or less even if said display 316 otherwise has the ability to use more than five display windows 505 to present image data 430C. The display 316 may communicate this limit to the user interface of the user's 405 computing entity 200, and the user interface may then limit how many application windows 505 a user 405 may choose to present therein. In another preferred embodiment, displays 412 may be configured such that only users 405 having certain permission levels 800 are allowed to transmit image data 430C thereto. For instance, a display 316 within a patient's 705B room may be configured such that only a single application window 505 of a patient's 705B computing entity 200 may be selected for presentation within said display user interface 316A, wherein said single application window cannot be streamed and/or mirrored; however, a healthcare professional 705A may be allowed to select a set number of application windows 505 for presentation via the display with one of those application windows 505 allowed to be mirrored and/or streamed.

In some preferred embodiments, indicia within the first user interface 410A and second user interface 411A may be used to indicate various types of patient data 430B to be presented within the display user interface 316A as image data 430C. For instance, a user 405 may be required to select four different types of patient data 430B from a selection screen of the patient's 705B user interface. The selection of these four types of patient data 430B may be used to create application windows 505, which the system 400 may convert into image data 430C and present via the display 316. The system 400 may use indicia to indicate which categories of patient data 430B are available for review, which may be decided based on permissions 800 of the system 400. In another preferred embodiment, indicia may be used to indicate which type of layout should be used by the display user interface 316A to present the patient data 430B thereon. Therefore, in some preferred embodiments, a user's 405 computing entity 200 may be used to control the layout of the display user interface 316A. For instance, a user 405 may manipulate the user interface in a way that commands the control board to select a layout having five display windows 605 representing one cell phone screen of a patient 705B and four tablet screens of a healthcare professional 705A, wherein the image data 430C presented in the five display windows 605 of the display user interface 316A corresponds with the image data 430C of the patient's 705B cell phone and the healthcare professional's 705A tablet, wherein the image data 430C corresponds to user data 430A and/or patient data 430B selected by the patient 705B and healthcare professional 705A via the user interfaces of their respective computing entities.

As mentioned previously, the database 115 may be configured to store image data 430C of the system 400; however, in some preferred embodiments, the same may act as a distributor of image data 430C to a display 316, wherein said display 316 may then present the image data 430C in a plurality of display windows 605 of the display user interface 316A. Alternatively, the processor 220 and/or database 115 may transmit image data 430C to a server 110, which may act as a distributor of image data 430C to the display 316. Therefore, in some preferred embodiments, the first computing device 410, second computing device 411, and display 316 may not be in direct communication with one another. Instead, the first computing device 410, second computing device 411, and display 316 may be connected via a secure network, wherein said secure network can only be accessed by a user 405 in close proximity to a hub of said secure network that allows said user 405 to access said network should said user 405 also have a permission level 800 that allows for access of said secure network. For instance, a hospital comprising the system 400 may have a secure network though which at least one of a first computing device 410 and second computing device 411 must communicate with at least one of a server 110 and database 115 before being allowed to communicate with a display 316 through said server 110 and database 115. This secured network may protect data of the system 400 from outside access and minimize security risks such as ransomware attacks.

In yet another preferred embodiment, the display user interface 316A may further comprise a communication window, which may allow a user 405 to remotely communicate with other users 405 of the system 400 while presenting patient data 430B 425B. For instance, a video feed captured by a camera of the first computing device 410 and second computing device 411 may be presented in a communication window of a display user interface 316A of a first display 316 and second display 316 along with any data within the plurality of display windows 705, wherein the plurality of display windows 705 of the display user interface 316A of the said second display 316 are configured to mirror data of the plurality of display windows 705 of said first display 316. This may allow a healthcare professional 705A to remotely interact with patients 705B and/or other healthcare professionals 705A while reviewing a patient's 705B patient data 430B 425B. For instance, a first healthcare professional 705A and second healthcare professional 705A collaborating in the treatment of a patient 705B may want to simultaneously meet with a patient 705B even when the second healthcare professional 705A is unable to be physically present with the first healthcare professional 705A and patient 705B. By way of a second video feed transmitting data to a communication window of a the first display user interface 316A of a first display 316 in the presence of said first healthcare professional 705A and patient 705B and a first video feed transmitting data to a communication window of a second display user interface 316A of a second display 316 in the presence of the second healthcare provider, the first healthcare provider, second healthcare provider, and patient 705B may all see the same data on their respective computing entity 200 as well as a live stream of each other so that they may collaborate. Therefore, the communication window may be used by the system 400 in multiple ways without departing from the inventive subject matter as described herein.

In some preferred embodiments, a user 405 may manipulate the user interface 410A, 411A of their computing entity 200 in a way that causes said user 405 to be entered into a queue so that they may interact with a healthcare professional 705A via said communication window. In one preferred embodiment, when a user 405 pairs their computing entity 200 to a display 316, the user interface 410A, 411A of the user's 405 computing entity 200 may present new options that may allow the user 405 to enter the display 316 into a queue. When a patient's 705B display 316 has its turn within the queue, the patient's 705B display 316 and healthcare professional's 705A display 316 pair so that communication may occur. In a preferred embodiment, communication occurs via image data 430C and audio data via a communication window; however, it is understood that other forms of communication, such as audio only and text, may occur without departing from the inventive subject matter described herein. In a preferred embodiment, a healthcare professional 705A may manage a queue in which a patient's 705B display 316 has entered by manipulating at least one of the display user interface 316A and first user interface 410A of the healthcare professional's 705A computing entity 200. For instance, a healthcare professional 705A may allow for the pairing of their display 316 with a patient's 705B display 316 by manipulating a "Start Appointment" indicia within the user interface 410A of said healthcare professional's 705A computing entity 200, which may cause the system 400 to execute programming instructions to pair the displays 316 and begin the appointment. In another preferred embodiment, a user 405 associated with a queue may indicate to the system 400 whether or not they are available. In one preferred embodiment, this may be accomplished with an indicia within the user interface 411A of the healthcare professional's 705A computing entity 200 that may be toggled by the healthcare professional 705A to describe said healthcare professional 705A as available or unavailable for sessions. For instance, a healthcare professional 705A may indicate that they are unavailable to take a session, which may cause the system 400 to at least one of pause the queue, give a session to another healthcare professional 705A, remove all displays 316 of patients 705B from that queue, etc.

In other preferred embodiments, the healthcare professional 705A may remotely enter a patient's 705B display 316 into a queue. For instance, a healthcare professional 705A may enter a patient's 705B display 316 into a queue approximately thirty minutes prior to a scheduled appointment with said patient 705B. Once again, this may be accomplished via the user interface 410A of the healthcare professional's 705A computing entity 200, wherein an "Add to Queue" indicia within said user interface 410A may cause the system 400 to execute programming instructions to enter the patient's 705B display 316 into a queue. In yet another preferred embodiment, the display 316 may automatically be entered into a queue based on patient data 430B within the system 400. For instance, if the patient 705B is required to have an appointment with a virtual patient 705B educator as part of the treatment protocol for the disease in which the patient 705B was diagnosed, the system 400 may automatically enter both the display 316 of the patient 705B and the display 316 of the virtual patient 705B educator into the relevant queue for the scheduled time.

A user 405 may add a queue to the system 400 via the user interface 410A, 411A if said user 405 has appropriate permissions. In one preferred embodiment, this may be accomplished by selecting a "Create New Queue" indicia within the user interface 410A, 411 of a computing entity 200 and subsequently inputting the required data. Data that may be required to create a queue may include, but is not limited to, queue name, user/group name, user email address, queue specialty, CPT/ICD-10 codes, or any combination thereof. The system 400 preferably keeps session records for sessions that are performed using displays 316 of healthcare professionals 705A and patients 705B. Data that may be included within session records may include, but are not limited to, patient 705B name, healthcare professional 705A name, patient 705B date of birth, date of session, time patient 705B entered queue, time patient 705B joined session, time session ended, image data 430C, audio data, or any combination thereof. In one preferred embodiment, the system 400 may track how long a healthcare professional 705A participated in each session and/or how long the patient 705B was engaged. In some preferred embodiments, machine learning techniques may be used to evaluate patient 705B engagement during a session.

In a preferred embodiment, the queue will appear differently with the user interfaces 410A, 411A of the system 400 based on permission levels 800 of the user 405. For instance, the user interface 410A presented to a healthcare professional 705A using the system 400 to view the queue preferably informs said healthcare professional 705A as to which patients 705B are in queue and in what order said patients 705B joined said queue. In other embodiments, the queue presented to a user 405 having appropriate permissions may additionally present data pertaining to each user 405 within the queue. In one preferred embodiment, this data may be used by a healthcare professional 705A to preview an upcoming session prior to accepting said session with a patient 705B. In a preferred embodiment, the patient 705B queue comprises an interactive list of informational widgets containing patient data 430B of users 405 who have been added to the queue. The informational widgets are preferably ordered by the time in which said patient's 705B display 316 was added to the queue. Data contained within an informational widget may include, but is not limited to, patient 705B name, patient 705B date of birth, patient 705B age, patient 705B sex, time in queue, patient 705B concerns/problems, procedures/labs completed for patient 705B, medications administered to patient 705B, patient 705B vital sign data, patient 705B device use history, or any combination thereof.

In a preferred embodiment, at least two healthcare professionals 705A having appropriate permissions must be logged into the system 400 and associated with a particular queue for said queue to be activated. Should only one healthcare professional 705A be logged into the system 400 and associated with a particular queue, the queue may be closed by the system 400 so that no additional displays 316 of patients 705B may be added to said queue. Further, some preferred embodiments of the system 400 may also prevent healthcare professionals 705A from adding displays 316 of patients 705B to said queue when said queue has been closed due to lack of needed personnel. Upon viewing the patient's 705B information within the informational widget, the healthcare professional 705A may choose to begin the session with the patient 705B, which will pair the displays 316 of the healthcare professional 705A and the patient 705B. In some preferred embodiments, a healthcare professional 705A may not begin a session until the patient's 705B information has been viewed. A patient 705B is preferably removed from the queue when a session is started by a healthcare professional 705A. In some preferred embodiments, when a first healthcare professional 705A and second healthcare professional 705A are viewing information of the same patient 705B and the second healthcare professional 705A attempts to create a session with a patient 705B who is already in a session with the first healthcare professional 705A, the system 400 may present a message to the second healthcare professional 705A to inform said second healthcare professional 705A that the patient 705B is already in a session and to please select another patient 705B.

In other preferred embodiments, a patient's 705B display 316 is automatically removed from a queue and associated with the display 316 of a healthcare professional 705A as soon as a healthcare professional 705A becomes available for a session. In such embodiments, it is preferable that the healthcare professional 705A be allowed to decide when to begin a session with the user 405. In some embodiments, the healthcare professional 705A may choose to unassociate a patient's 705B display 316 with their own, which may cause the system 400 to reinsert the display 316 of the patient 705B into the queue. When a patient's 705B display 316 is unassociated in this manner, the system 400 preferably gives the unassociated display 316 of the patient 705B priority over other displays 316 within the queue. For instance, a healthcare professional 705A may toggle an indicia with one of the user interface 410A of the computing entity 200 of said healthcare professional 705A or the display user interface 316A of the display 316 of said healthcare professional 705A, causing the system 400 to execute program instructions that remove the display 316 of healthcare professional 705A from the queue. Any display 316 of a patient 705B that was previously removed from the queue and associated with the healthcare professional's 705A display 316 may automatically be unassociated with the healthcare professional's 705A display 316, subsequently reinserted back into said queue, and grated top priority within said queue.

The various user interfaces of the system 400 may be configured to provide different functionality to the user 405 based on what the user 405 is doing. As such, the display user interfaces 316A and/or the user interfaces 410A, 411A of the system 400 may allow for different functionality depending on activities in which the users 405 of the system 400 are engaged in. For instance, a patient 705B resting in their room with no scheduled medical evaluations/appointments with a healthcare professional 705A may be permitted by the display user interface 316A to view cable television, educational material, and play games. For instance, a patient 705B who has been entered into a queue for a medical evaluation/appointment with a medical professional may only be permitted by the display user interface 316A to view educational material. For instance, a patient 705B using the system 400 during a scheduled medical evaluation/appointment with a healthcare professional 705A via the communication window may be unable to manipulate the display user interface 316A but may be allowed to manipulate the user interface of their computing entity 200 so that they may access patient data 430B to present within an application window.

To prevent un-authorized users 405 from accessing other users' 405 information, the system 400 may employ a security method. As illustrated in FIG. 8, the security method of the system 400 may comprise a plurality of permission levels 800 that may grant users 405 access to user content 815, 835, 855 within the system 400 while simultaneously denying users 405 without appropriate permission levels 800 the ability to view user content 815, 835, 855. To access the user content 815, 835, 855 stored within the system 400, users 405 may be required to make a request via a user interface. Access to the data within the system 400 may be granted or denied by the processor 220 based on verification of a requesting user's 805, 825, 845 permission level 800. If the requesting user's 805, 825, 845 permission level 800 is sufficient, the processor 220 may provide the requesting user 805, 825, 845 access to user content 815, 835, 855 stored within the system 400. Conversely, if the requesting user's 805, 825, 845 permission level 800 is insufficient, the processor 220 may deny the requesting user 805, 825, 845 access to user content 815, 835, 855 stored within the system 400. In an embodiment, permission levels 800 may be based on user roles 810, 830, 850 and administrator roles 870, as illustrated in FIG. 8. User roles 810, 830, 850 allow requesting users 805, 825, 845 to access user content 815, 835, 855 that a user 405 has uploaded and/or otherwise obtained through use of the system 400. Administrator roles 870 allow administrators 865 to access system 400 wide data.

In an embodiment, user roles 810, 830, 850 may be assigned to a user in a way such that a requesting user 805, 825, 845 may view user profiles 430 containing user data 430A, patient data 430B, and image data 430C via a user interface. To access the data within the system 400, a user 405 may make a user request via the user interface to the processor 220. In an embodiment, the processor 220 may grant or deny the request based on the permission level 800 associated with the requesting user 805, 825, 845. Only users 405 having appropriate user roles 810, 830, 850 or administrator roles 870 may access the data within the user profiles 430. For instance, as illustrated in FIG. 8, requesting user 1 805 has permission to view user 1 content 815 and user 2 content 835 whereas requesting user 2 825 only has permission to view user 2 content 835. Alternatively, user content 815, 835, 855 may be restricted in a way such that a user may only view a limited amount of user content 815, 835, 855. For instance, requesting user 3 845 may be granted a permission level 800 that only allows them to view user 3 content 855 related to their specifically to their healthcare records within the EHR but not other data considered user 3 content 855. In the example illustrated in FIG. 8, an administrator 865 may bestow a new permission level 800 on users 405, allowing said administrator 865 to grant said users 405 greater permissions or lesser permissions. For instance, an administrator 865 having an administrator role 870 may bestow a greater permission level 800 on other users so that they may view user 3's content 855 and/or any other user's 405 content 815, 835, 855. Therefore, the permission levels 800 of the system 400 may be assigned to users 405 in various ways without departing from the inventive subject matter described herein.

FIG. 9 provides a flow chart 900 illustrating certain, preferred method steps that may be used to carry out the method of pairing a computing entity 200 with a display 316 and presenting image data 430C containing at least one of user data 430A and patient data 430B via a display user interface 316A. Step 905 indicates the beginning of the method. During step 910, the processor may receive a computer readable signal from a computing entity 200, wherein said computer readable signal contains instructions asking to connect said computing entity 200 to a display 316. The processor may then perform a query during step 915 to determine if a permission level 800 of said computing entity 200 is sufficient to allow said computing entity 200 access to said display, wherein said permission level 800 is preferably contained within said computer readable signal. Based on the results of the query, the processor may take an action during step 920. If the processor determines that the computing entity 200 does not have appropriate permissions to connect to said display, the processor may proceed to the terminate method step 950. If the processor determines that the computing entity 200 does have appropriate permission to connect to said computing entity 200 the processor may proceed to step 925, wherein the computing entity 200 may connect to the display.

Once connected, the processor may receive image data 430C pertaining to application windows of a user interface of the computing entity 200 from said computing entity 200 during step 930, wherein said image data 430C contains at least one of user data 430A and patient data 430B pertaining to a user 405 of the system 400. In a preferred embodiment, if more than one application window containing patient data 430B is transferred in the form of image data 430C to said display, only one of said image data 430C may be in the form of a video feed. After receiving the image data 430C, the processor may match the image data 430C with a layout of a display user interface 316A during step 935. The processor may then present the display user interface 316A during step 940 and subsequently present the image data 430C within the display user interface 316A during step 945. Once presented, the system 400 may proceed to the terminate method step 950.

FIG. 10 provides a flow chart 1000 illustrating certain, preferred method steps that may be used to carry out the method of entering a session using the system 400. During step 1005, the processor may facilitate the pairing between a computing entity 200 of a first user with the display, wherein said first user may use a user interface of said computing entity 200 to cause said pairing. Once paired, the processor may display a QR code that may be scanned by a computing entity 200 of a second user during step 1010. Once scanned, the processor may perform a query to determine if a camera of the display will be activated during step 1015. Based on the results of the query, the processor may perform an action during step 1020. If the processor determines that the camera is not to be activated, the system 400 may proceed to the terminate method step 1055. If the system 400 determines that the camera is to be activated, the system 400 may activate the camera during step 1025. In a preferred embodiment, the system 400 may ask a first user whether to activate the camera of the display on at least one of the user interface 410A, 411A of the user's computing entity 200 or the display user interface 316A of the display 316.

Once the camera has been activated, the system 400 may use session data to enter the display into a queue during step 1030. In a preferred embodiment, the queue is an order in which the display of the first user will be operably connected with a display of a third user. A plurality of displays 316 may be entered into the queue by the system 400. The system 400 may then count down the queue during step 1035 and perform a query during step 1040 to determine whether to connect the display 316 of the first user with the display 316 of the second user. Based on the results of the query, the system 400 may perform an action during step 1045. If the system 400 determines to not connect the display 316 of the first user with the display 316 of the second user based on the queue, the system 400 may return to step 1035. If the system 400 determines to connect the display 316 of the first user with the display 316 of the second user based on the queue, the system 400 may facilitate the transfer of image data 430C from the camera of the first user to the display 316 of the third user during step 1050. In some preferred embodiments, a camera of the display 316 of the third user may be activated by the system 400 so that image data 430C may be sent from the display 316 of the third user to the display 316 of the first user. Once the displays 316 of the first user and third user have been operably connected, the system 400 may proceed to terminate method step 1055.

FIG. 11 provides a flow chart 1100 illustrating certain, preferred method steps that may be used to carry out the method of starting a session using the system 400. During step 1105, the processor may facilitate the pairing between a computing entity 200 of a first user with a display 316, wherein said first user may use a user interface of said computing entity 200 to cause said pairing. Once paired, the processor may enter the display 316 of the first user into a receiving queue of the system 400 during step 1110. In one preferred embodiment, the processor may automatically enter a display 316 of a user 405 into a receiving queue based on user data 430A and user permissions. In another preferred embodiment, the user 405 may select within a user interface 410A, 411A of their computing entity 200 when to enter a receiving queue of the system 400. Once entered into the receiving queue, the system 400 may perform a query during step 1015 to determine if there is a display 316 of a second user that has been placed within a requesting queue. Based on the results of the query, the system 400 may take an action during step 1020. If it is determined that a display 316 of second user has not been placed in the requesting queue, the system 400 may return to step 1015 during step 1025. If it is determined that a display 316 of second user has been placed in the requesting queue, the system 400 may operably connect the display 316 of said second user with said display 316 of said first user during step 1030. Once the system 400 has operably connected the display of the first user with the display of the second user, the system 400 may proceed to terminate method step 1035.

The subject matter described herein may be embodied in systems, apparati, methods, and/or articles depending on the desired configuration. In particular, various implementations of the subject matter described herein may be realized in digital electronic circuitry, integrated circuitry, specially designed application specific integrated circuits (ASICs), computer hardware, firmware, software, and/or combinations thereof. These various implementations may include implementation in one or more computer programs that may be executable and/or interpretable on a programmable system including at least one programmable processor, which may be special or general purpose, coupled to receive data and instructions from, and to transmit data and instructions to, a storage system, and at least one peripheral device.

These computer programs, which may also be referred to as programs, software, applications, software applications, components, or code, may include machine instructions for a programmable processor, and may be implemented in a high-level procedural and/or object-oriented programming language, and/or in assembly machine language. As used herein, the term "non-transitory computer-readable medium" refers to any computer program, product, apparatus, and/or device, such as magnetic discs, optical disks, memory, and Programmable Logic Devices (PLDs), used to provide machine instructions and/or data to a programmable processor, including a non-transitory computer-readable medium that receives machine instructions as a computer-readable signal. The term "computer-readable signal" refers to any signal used to provide machine instructions and/or data to a programmable processor. To provide for interaction with a user, the subject matter described herein may be implemented on a computer having a display, such as a cathode ray tube (CRD), liquid crystal display (LCD), light emitting display (LED) monitor for displaying information to the user and a keyboard and a pointing device, such as a mouse or a trackball, by which the user may provide input to the computer. Displays may include, but are not limited to, visual, auditory, cutaneous, kinesthetic, olfactory, and gustatory displays, or any combination thereof.

Other kinds of devices may be used to facilitate interaction with a user as well. For instance, feedback provided to the user may be any form of sensory feedback, such as visual feedback, auditory feedback, or tactile feedback; and input from the user may be received in any form including, but not limited to, acoustic, speech, or tactile input. The subject matter described herein may be implemented in a computing system that includes a back-end component, such as a data server, or that includes a middleware component, such as an application server, or that includes a front-end component, such as a client computer having a graphical user interface or a Web browser through which a user may interact with the system described herein, or any combination of such back-end, middleware, or front-end components. The components of the system may be interconnected by any form or medium of digital data communication, such as a communication network. Examples of communication networks may include, but are not limited to, a local area network ("LAN"), a wide area network ("WAN"), metropolitan area networks ("MAN"), and the internet.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For instance, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, devices, and arrangements of the parts and method stages which have been described and illustrated in order to explain the nature of this inventive subject matter can be made without departing from the principles and scope of the inventive subject matter.

What is claimed is:

1. A system for managing data transferred between computing devices and displays:
a first computing device having a first user interface,
wherein said first computing device is configured to transform at least one application window of said first user interface into first image data,
a second computing device having a second user interface,
wherein said second computing device is configured to transform said at least one application window of said second user interface into second image data,
a first display having a control board operably connected to said first computing device and said second computing device,
wherein a processor of said control board is configured to receive said first image data from said first computing device,
wherein a processor of said control board is configured to receive said second image data from said second computing device,
wherein said processor of said control board presents said first image data and said second image data in a plurality of display windows of a display user interface of said first display, and
a non-transitory computer-readable medium coupled to said processor,
wherein said non-transitory computer-readable medium contains instructions stored thereon, which, when executed by said processor, cause said processor to perform operations comprising:
receiving said first image data of said at least one application window from said first computing device,
receiving said second image data of said at least one application window from said second computing device,
determining a layout of said display user interface based on said first image data and second image data, and
presenting said layout containing said first image data and said second image data via said first display.

2. The system of claim 1, wherein said first image data contains at least one of user data and patient data of a first user profile, wherein said second image data contains at least one of said user data and said patient data of a second user profile.

3. The system of claim 1, wherein at least one of said first image data and said second image data is a video stream.

4. The system of claim 3, wherein said video stream is of an active application window of said at least one application window of said first user interface.

5. The system of claim 4, wherein said active application window is an application window in which a user is manipulating within said first user interface.

6. The system of claim 1, further comprising a database operably connected to said processor.

7. The system of claim 6, further comprising additional instructions stored on said non-transitory computer-readable medium, which, when executed by said processor, cause said processor to perform additional operations comprising:
saving a video stream of said display user interface containing said first image data and said second image data in at least one of said non-transitory computer-readable medium and said database.

8. The system of claim 1, further comprising a first camera operably connected to said first display,
wherein said first camera is configured to obtain a plurality of image data of a first user using said first display, first computing device, and first camera.

9. The system of claim 8, further comprising a second display operably connected to said processor and said second computing device,
wherein said second display is configured to receive said plurality of image data from said first camera of said first display and present said plurality of image data within a communication window of said display user interface of said second display, and
wherein said processor of said control board of said second display is configured to receive said second image data from said second computing device.

10. The system of claim 9, further comprising a second camera operably connected to said second display,
wherein said second camera is configured to obtain said plurality of image data of a second user using said second display, second computing device, and second camera, and
wherein said first display is configured to receive said plurality of image data from said second camera of said second display and present said plurality of image data within said communication window of said display user interface of said first display.

11. A system for managing data transferred between computing devices and displays:
a first computing device having a first user interface,
wherein said first computing device is configured to transform at least one application window of said first user interface into first image data,
a second computing device having a second user interface,
wherein said second computing device is configured to transform said at least one application window of said second user interface into second image data,
a third computing device having a third user interface,
wherein said third computing device is configured to scan a barcode of a display so that said display is entered into a queue,
a first display having a control board and first camera operably connected to said first computing device,
wherein a processor of said control board is configured to receive said first image data from said first computing device,
wherein said first camera is configured to obtain a plurality of image data of a first user using said first display, first computing device, and first camera,
wherein said processor of said control board presents said first image data and said second image data in a plurality of display windows of a display user interface of said first display,
a second display having a control board and second camera operably connected to said first computing device,
wherein said processor of said control board is configured to receive said second image data from said second computing device,
wherein said second camera is configured to obtain said plurality of image data of a second user using said second display, second computing device, and second camera, wherein said processor of said control board presents said first image data and said second image data in said plurality of display windows of said display user interface of said second display, and a non-transitory computer-readable medium coupled to said processor,
wherein said non-transitory computer-readable medium contains instructions stored thereon, which, when executed by said processor, cause said processor to perform operations comprising:
receiving said first image data of said at least one application window from said first computing device,
receiving said second image data of said at least one application window from said second computing device,
entering said first display into a queue when said barcode is scanned by said third computing device,
connecting said first display with said second display,
determining a layout of said display user interface based on said first image data, second image data, and plurality of image data, and
presenting said layout containing said first image data, second image data, and plurality of image data on said first display and said second display.

12. The system of claim 11, wherein said first image data contains at least one of user data and patient data of a first user profile, wherein said second image data contains at least one of said user data and said patient data of a second user profile.

13. The system of claim 11, wherein at least one of said first image data and said second image data is a video stream.

14. The system of claim 13, wherein said video stream is of an active application window of said at least one application window of said second user interface.

15. The system of claim 14, wherein said active application window is said at least one application window in which a user is manipulating within said second user interface.

16. The system of claim 11, further comprising a database operably connected to said processor.

17. The system of claim 16, further comprising additional instructions stored on said non-transitory computer-readable medium, which, when executed by said processor, cause said processor to perform additional operations comprising:
saving a video stream of said display user interface containing said first image data and said second image data in at least one of said non-transitory computer-readable medium and said database.

18. The system of claim 11, wherein said first display presents said barcode that is scannable using said third computing device.

19. The system of claim 11, further comprising additional instructions stored on said non-transitory computer-readable medium, which, when executed by said processor, cause said processor to perform additional operations comprising:
presenting said barcode on said first display, and
determining when said barcode is scanned using said third computing device.

20. A method for presenting patient data comprising steps of:
obtaining a first computing device having a first user interface,
wherein said first computing device is configured to transform at least one application window of said first user interface into first image data,
obtaining a second computing device having a second user interface,
wherein said second computing device is configured to transform said at least one application window of said second user interface into second image data,
obtaining a first display configured to present said first image data and second image data within display windows of a display user interface,
logging into a first user profile using said first user interface,
logging into a second user profile using said second user interface,
creating at least one said at least one application window within said first user interface using at least one of patient data and user data of said first user profile,
creating at least one said at least one application window within said second user interface using at least one of said patient data and said user data of said second user profile,
selecting which at least one application window of said first computing device to transmit to said first display,
wherein selecting said at least one application window within said first user interface causes said first computing device to transform said at least one application window into first image data,
wherein said first image data is transmitted to said first display to be presented within said display user interface, and
selecting which at least one application window of said second computing device to transmit to said first display,
wherein selecting said at least one application window within said second user interface causes said second computing device to transform said at least one application window into second image data,
wherein said second image data is transmitted to said first display to be presented within said display user interface.

21. The method of claim 20, further comprising additional steps of:
interacting with one of said at least one application window of said second computing device,
wherein interaction with said at least one application window causes said second computing device to create a video stream of said first image data.

22. The method of claim 20, wherein said first image data contains at least one of user data and patient data of a first user profile, wherein said second image data contains at least one of said user data and said patient data of a second user profile.

23. The method of claim 20, further comprising additional steps of:
obtaining a third computing device having a third user interface,
wherein said third user interface is configured to scan a barcode that places said first display in a queue, and
scanning said barcode presented on said first display using said third computing device.

24. The method of claim 23, wherein said first display is placed in a queue when said third computing device scans said barcode presented on said first display.

25. The method of claim 23, further comprising additional steps of:

verifying activation of a camera of said first display using at least one of said first computing device and said first display.

26. The method of claim 25, further comprising additional steps of:

obtaining a second display configured to present said first image data and second image data within display windows of a display user interface.

27. The method of claim 26, further comprising additional steps of:

verifying activation of a camera of said second display using at least one of said second computing device and said second display.

\* \* \* \* \*